United States Patent [19]

Smith

[11] Patent Number: 5,366,980
[45] Date of Patent: Nov. 22, 1994

[54] USE OF DEXTROMETHORPHAN AND AN OXIDASE INHIBITOR TO TREAT DERMATITIS

[76] Inventor: Richard A. Smith, 7569 Cabrillo Ave., La Jolla, Calif. 92037

[21] Appl. No.: 114,845

[22] Filed: Sep. 2, 1993

Related U.S. Application Data

[63] Continuation-in-part of Ser. No. 896,053, Jun. 9, 1992, abandoned, which is a continuation-in-part of Ser. No. 859,105, Mar. 27, 1992, Pat. No. 5,206,248, and Ser. No. 717,424, Jun. 17, 1991, Pat. No. 5,166,207.

[51] Int. Cl.$^5$ ............................................. A61K 31/445
[52] U.S. Cl. .................................................... 514/289
[58] Field of Search ......................................... 514/289

[56] References Cited

U.S. PATENT DOCUMENTS 5,166,207 11/1992 Smith .................................. 514/270
5,206,248 4/1993 Smith .................................. 514/289

OTHER PUBLICATIONS

Koppel, C., et al, "Urinary metabolism of dextromethorphan in man," *Arzneim.-Forsch./Drug Research* 37:1304–1306 (1987).

Guttendorf, R. J., et al, "Simplified phenotyping with dextromethorphan by thin-layer chromatography," *Ther. Drug. Monit.* 10:490–498 (1988).

Kupfer, A., et al, "Dextromethorphan as a safe probe for debrisoquine hydroxylation polymorphism," *Lancet:* 517–518 (Sep. 1, 1984).

*Physician's Desk Reference*, 44th Edition (1990), pp. 670–671 (Medical Economics Company, 1990).

Inaba, T., et al, "In vitro inhibition studies of two isozymes of human liver cytochrome P-450," *Drug Metabolism and Diposition* 13: 443–447 (1985).

Inbaba, T., et al, "Quinidine: Potent inhibition of sparteine and debrisoquin oxidation in vivo," *Br. J. Clin. Pharmacol.* 22: 199–200 (1986).

Broly, F., et al, "Effect of quinidine on the dextromethorphan O-methylase activity of microsomal fractions from human liver," *Br. J. Clin. Pharmacol.* 28: 29–36 (1989).

Broly, F., et al., "Inhibitory studies of mexiletine and dextromethorphan oxidation in human liver microsomes," *Biochem. Pharmacol.* 39: 1045–1053 (1990).

Brinn, R., et al, "Sparteine oxidation is practically abolished in quinidine–treated patients," *Br. J. Clin. Pharmacol.* 22: 194–197 (1986).

Brosen, K., et al, "Extensive metabolizers of debrisoquin become poor metabolizers during quinidine treatment," *Pharmacol. Toxicol.* 60: 312–314 (1987).

Nielsen, M. D., et al, "A dose–effect study of the in vivo inhibitory effect of quinidine on sparteine oxidation in man," *Br. J. Clin. Pharmacol.* 29: 299–304 (1990).

Walker, E. O., and Hunt, V. P., "An open label trial of dextromethorphan in Huntington's Disease," *Clin. Neuropharmacol.* 12: 322–330 (1989).

Albers, G. W., et al, "Safety and tolerance of oral dextromethorphan in patients at risk for brain ischemia," *Stroke* 22: 1075–1077 (1991).

Applebaum, J. S., et al, "Dextromethorphan in the treatment of ALS: A Pilot Study," Abstract number 960S (p. 393) in *Neurology 41 (Suppl. 1)*, Mar. 1991.

*Primary Examiner*—Richard L. Raymond
*Attorney, Agent, or Firm*—Patrick D. Kelly

[57] ABSTRACT

This invention discloses a method for treating human patients suffering from dermatitis, particularly severe dermatitis which does not respond adequately to non-prescription drugs. Such patients are treated using dextromethorphan (DM), an antitussive agent normally used in cough syrup. If the patient is a so-called "extensive metabolizer," an antioxidant drug (such as quinidine) can be coadministered to inhibit the DM-degrading activity of debrisoquin hydroxylase, an enzyme that will rapidly convert DM into its metabolite, dextrorphan. This treatment has been shown to be highly effective in treating severe dermatitis, and in most patients this drug combination causes no significant adverse side effects.

5 Claims, 2 Drawing Sheets

DEGRADATION OF DEXTROMETHORPHAN

USE OF DEXTROMETHORPHAN AND AN OXIDASE INHIBITOR TO TREAT DERMATITIS

RELATED APPLICATIONS

This is a continuation-in-part of application Ser. No. 07/896,053, filed Jun. 9, 1992, now abandoned, which in turn is a continuation-in-part of application Ser. No. 07/859,105, filed Mar. 27, 1992, now U.S. Pat. No. 5,206,248, and of application Ser. No. 07/717,424, filed Jun. 17, 1991, now U.S. Pat. No. 5,166,207.

BACKGROUND OF THE INVENTION

This invention relates to pharmacology, and to the use of dextromethorphan in conjunction with a second drug that inhibits enzymatic oxidation of dextromethorphan.

Dextromethorphan (frequently abbreviated as DM) is the common name for (+)-3-methoxy-N-methylmorphinan. It is a non-addictive opioid comprising a dextrorotatory enantiomer (mirror image) of the morphinan ring structure which forms the molecular core of most opiates. DM is widely used as an antitussive agent (i.e., as a cough suppressant) in over-the counter formulations such as cough syrup. It is also being evaluated as a possible treatment for certain types of excitotoxic brain damage caused by ischemia (low blood flow) and hypoxia (inadequate oxygen supply), which are caused by events such as stroke, cardiac arrest, and asphyxia. This anti-excitotoxic activity is discussed in items such as Choi 1987 (full citations to articles are provided below), Wong et al 1988, Steinberg et al 1988, and U.S. Pat. No. 4,806,543 (Choi 1989).

The antitussive activity of DM is believed to be due primarily to its activity at a class of neuronal receptors known as sigma receptors. These receptors are inhibitory, which means that activation of these receptors suppresses certain types of nerve signals. Sigma receptors are often referred to as sigma opiate receptors, but there is some question as to whether they are true opiate receptors, so many researchers refer to them simply as sigma receptors. Some researchers refer to "high-affinity dextromethorphan receptors;" this category apparently includes but may not be limited to sigma receptors.

The anti-excitotoxic effects of DM are believed to be primarily due to its activity at another class of receptors known as N-methyl-D-aspartate (NMDA) receptors, which are one type of excitatory amino acid (EAA) receptor. Unlike its agonist activity at sigma receptors, DM acts as an antagonist at NMDA receptors, which means that DM suppresses the transmission of nerve impulses mediated via NMDA receptors, Since NMDA receptors are excitatory receptors, the activity of DM as an NMDA antagonist also leads to the suppression of certain types of nerve signals.

Because of its activity as an NMDA antagonist which may be able to block excitotoxic damage to neurons, DM is also of interest as a potential treatment for neurodegenerative diseases, including Parkinson's disease, Alzheimer's disease, and amyotrophic lateral sclerosis (ALS, also called Lou Gehrig's disease), all of which are suspected of containing an excitotoxic aspect of their etiology. Reports of this field of research include Walker and Hunt 1989, Albers et al 1991, and Applebaum et al 1991.

Dextromethorphan has also been reported to suppress neural activity mediated by neuronal calcium channels (Carpenter et al 1988).

Because DM activity apparently involves at least three classes of neuronal receptors, it is difficult to clearly attribute the effects of DM in suppressing nerve impulses to a single type of receptors. Nevertheless, the chemistry and structure of DM are well-known, and the pharmacology is described in standard texts such as Goodman and Gilman's *Pharmacological Basis of Therapeutics* and Rodd 1960, and in articles such as Tortella et al 1989, Leander 1989, Koyuncuoglu & Saydam 1990, Ferkany et al 1988, George et at 1988, Prince & Feeser 1988, Feeser et al 1988, Craviso and Musacchio 1983, and Musacchio et al 1988.

Dextromethorphan Metabolism

As mentioned above, DM is being studied as a possible treatment for neurodegenerative diseases such as Parkinson's disease, Alzheimer's disease, and ALS. Accordingly, the Applicant, a neurologist who specializes in working with ALS patients, undertook a study of DM to determine whether it might be able to retard the progress of ALS.

Regrettably, DM was not able to slow down the progressive loss of strength, slurring of speech, and other muscular symptoms suffered by those patients. However, during the course of that study, other important findings emerged, as discussed below.

Figure 1:
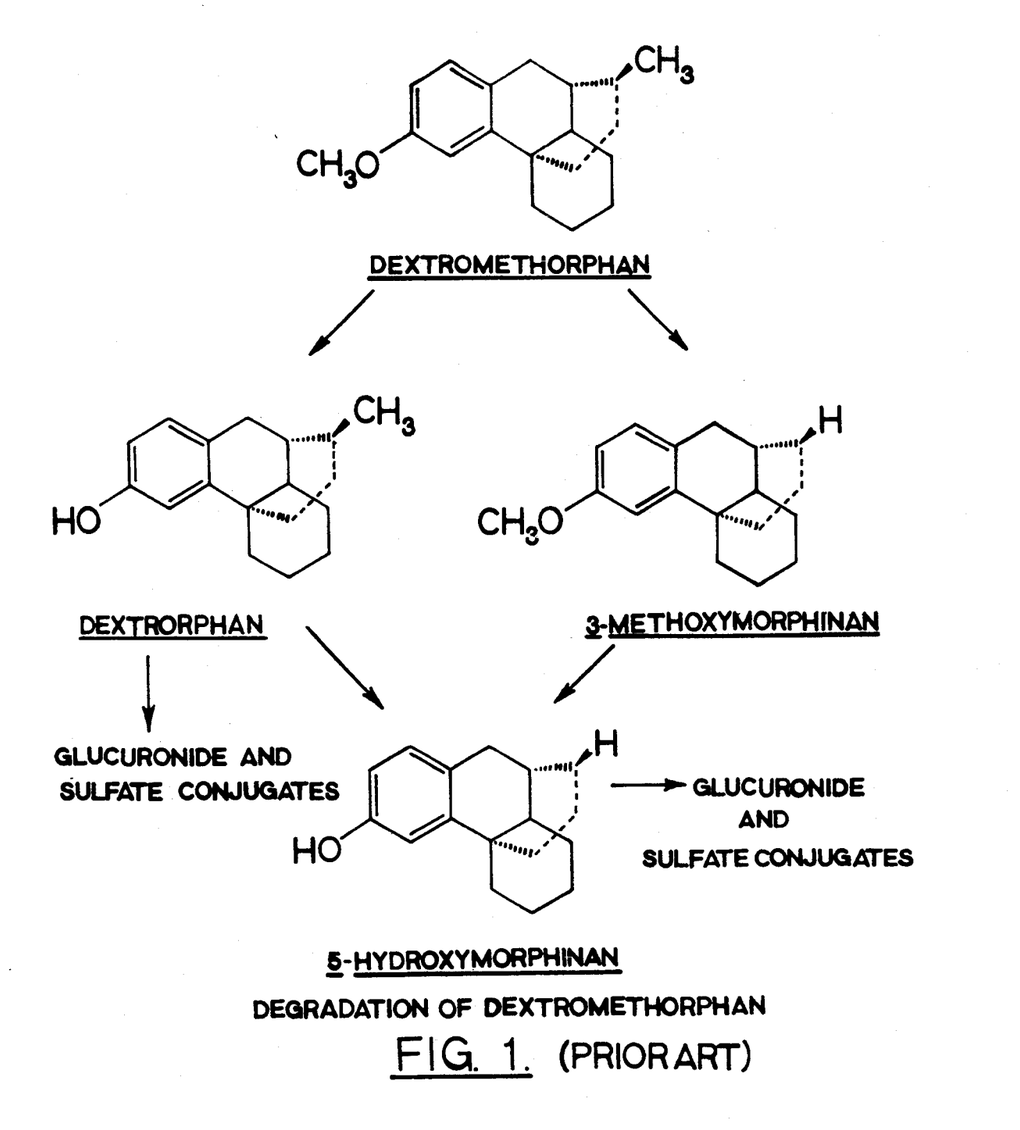
FIG. 1 is a depiction of the metabolic pathways involved in the degradation and elimination of dextromethorphan.

Before his study began, the Applicant was aware that in most people, DM disappears fairly rapidly from the bloodstream (see, e.g., Vetticaden et al 1989 and Ramachander et al 1977). DM is converted in the liver to two metabolites called dextrorphan and 3-methoxymorphinan, by an enzymatic process called O-demethylation; in this process, one of the two pendant methyl groups is replaced by hydrogen. If the second methyl group is removed, the resulting metabolite is called 5-hydroxymorphinan. Dextrorphan and 5-hydroxymorphinan are covalently bonded to other compounds in the liver (primarily glucuronic acid or sulfur-containing compounds such as glutathione) to form glucuronide or sulfate conjugates which are eliminated fairly quickly from the body via urine. These metabolic pathways are shown in FIG. 1.

During his initial studies, the Applicant confirmed that the normal processes of rapid oxidation and elimination occur in most ALS patients. No difference in the metabolism of dextromethorphan was detected in ALS patients compared to data previously reported for healthy adults.

The rapid metabolism of DM makes it very difficult to correlate DM quantities administered to a patient, with DM quantities circulating in the patient's blood. Since the Applicant wanted to stabilize blood concentrations of DM in order to improve the significance and reliability of any results in ALS patients, he did a literature search on the metabolic pathways that cause DM to disappear from the bloodstream. That search quickly identified a particular enzyme that is primarily responsible for DM oxidation. In most articles, this enzyme is usually referred to as debrisoquin hydroxylase; it was discovered some years ago to carry out a hydroxylation reaction on debrisoquin. It is sometimes referred to as $P450_{DB}$ or as P450-2D6, and it apparently is identical to an enzyme called sparteine monooxygenase, which was shown years ago to metabolize sparteine. It was not until recently that scientists realized that a single isozyme appears to be primarily responsible for oxidizing both debrisoquin and sparteine, as well as dextromethorphan and various other substrates.

Debrisoquin hydroxylase belongs to a family of enzymes known as cytochrome P450 enzymes, or as cytochrome oxidase enzymes. These enzymes are found at high concentrations in liver cells (primarily in microsomes, which are organelles inside the liver cells), and at lower concentrations in various other organs and tissues such as the lungs; see, e.g., Fonne-Pfister et al 1987 and Niznik et al 1990. By oxidizing lipophilic compounds, cytochrome oxidase enzymes help eliminate compounds that would otherwise act as toxins or accumulate to undesired levels. Oxidation renders lipophilic compounds more soluble in water, which helps the body eliminate them in urine or in aerosols exhaled from the lungs.

A follow-up literature search by the Applicant revealed that a number of compounds inhibit the activity of debrisoquin hydroxylase (sparteine monooxygenase); see Inaba et al 1985. The most powerful of these inhibitors is quinidine, a dextrorotatory stereoisomer of quinine, normally used to treat cardiac arrhythmias. Inaba et al 1986 and Nielsen et al 1990 discuss the ability of quinidine to inhibit the oxidation of sparteine in in vivo animal tests, and Brinn et al 1986, Brosen et al 1987, and Broly et al 1989 discuss the ability of quinidine to inhibit DM metabolism in liver cell preparations.

After studying the Inaba et al 1985 article, which rated quinidine as the most potent inhibitor of the sparteine monooxygenase enzyme, and after recognizing that the sparteine monooxygenase enzyme appears to be the same enzyme referred to elsewhere as debrisoquin hydroxylase, the Applicant realized that quinidine might be a useful adjunct for co-administration with DM in order to prolong the life and increase the concentration of DM in the circulating blood of so-called "extensive metabolizers." When he tested that hypothesis using quinidine in conjunction with DM (both administered orally), the Applicant discovered that quinidine does indeed have a pronounced effect in increasing and stabilizing the quantity of DM circulating in the blood. That discovery is discussed in U.S. Pat. No. 5,166,207, which was also invented by the Applicant; the teachings of that patent are incorporated by reference.

The Applicant also discovered that DM in conjunction with quinidine had a remarkable and unexpected side effect: it was highly effective in reducing the symptoms of "emotional lability" (also referred to as "emotional incontinence") in several ALS patients involved in the test. Emotional lability is a complex problem in which patients suffering from neurological damage (typically due to a stroke or head injury or a neurologic disease such as ALS or Alzheimer's disease) become unable to control spasmodic emotional outbursts such as explosive laughing or uncontrollable weeping. This discovery involving emotional lability is discussed in U.S. Pat. No. 5,206,248, which was also invented by the Applicant; the contents of that patent are incorporated by reference. Additional patients treated with the combined DM/antioxidant regimen since the filing of that application have reported that this newly discovered use is highly effective and beneficial.

The unexpected benefit in treating emotional lability was not observed in any patients who received DM alone. All patients who became involved in the study initially received DM and/or quinidine alone, to ensure that these drugs would not adversely affect them. The drugs were coadministered only after a tolerance and/or dosage range for one drug had been established for a patient. The benefits of either drug alone in suppressing emotional lability did not become apparent until after a patient began taking both drugs together.

Subsequently, the Applicant discovered another completely unexpected benefit which arose from administering DM in conjunction with quinidine to another ALS patient who was an extensive metabolizer. She had suffered for over ten years from a severe dermatologic problem which had been diagnosed as lichen planus. It was characterized by numerous discolored lesions on her abdomen and legs, which itched severely and were rather painful. She had been prescribed numerous medications by skin specialists, including steroids to control swelling and various analgesics and antidepressants to help relieve the pain and itching and to help her sleep; none had provided any substantial relief. Within two months after beginning a regimen of both quinidine and DM, she had obtained major relief from the itching and pain. The lesions also subsided, and within another two months the lesions almost completely healed with no apparent scarring.

After discovering this unexpected result, the Applicant disclosed it in confidence to another physician/researcher who specializes in dermatology, who is carrying out preliminary tests on other patients who suffer from severe or intractable dermatitis. The results obtained thus far, although only preliminary, indicate that in extensive metabolizers, a combination of DM with an antioxidant that suppresses oxidation of DM appears to be effective in treating such dermatitis.

The Prior Art re: Anti-Oxidants

The unexpected discovery that a combination of DM and quinidine could reduce emotional lability in ALS patients caused the Applicant to focus careful attention on the prior art which discussed both DM and antioxidant drugs. During a study of the prior art, a question repeatedly occurred to him: since quinidine and certain other antioxidant drugs have been known for years to suppress the metabolism of DM, why hadn't anyone else ever administered quinidine or other antioxidants as a way to increase DM concentrations in the blood of patients being treated with DM?

The answer to that question emerged when several previously unrelated facts were correlated:

1. A substantial fraction of the general public (roughly 7 to 10%) does not have a properly functioning gene which encodes the debrisoquin hydroxylase enzyme.

2. People who do not have the properly functioning debrisoquin hydroxylase enzyme are classified and referred to by doctors and pharmacologists as "poor metabolizers" (this term is used in articles such as Kupfer et al 1984 and Guttendorf et al 1988). Such patients are regarded as somewhat high-risk patients who must be treated with special care and attention, since they are overly sensitive to certain drugs that can be prescribed safely to people who have the full set of cytochrome P450 enzymes (such people are usually referred to as "extensive metabolizers" or "good metabolizers").

3. In addition to the inhibition of debrisoquin hydroxylase, which is exceptionally potent and easily demonstrated, other cytochrome P450 isozymes are also likely to be suppressed by quinidine, with varying levels of binding affinity. Cytochrome P450 enzymes are notoriously non-specific; a single isozyme can react with numerous substrates having widely different chemical structures, and various isozymes are known to have overlapping activity on a single substrate. This is consistent with their role in eliminating lipophilic toxins, and it is illustrated by the ability of debrisoquin hydroxylase to metabolize numerous different substrates, including dextromethorphan, debrisoquin, and sparteine (which have very different structures). Accordingly, even though quinidine exerts its most marked effect on debrisoquin hydroxylase, it is likely to suppress a number of other cytochrome P450 enzymes as well, thereby subjecting a patient to a more general loss of normal and desirable metabolic activity.

4. Since DM is a relatively safe drug which can be administered without a prescription, it is often used as a convenient tool (often called a probe drug) during clinical tests to determine whether a patient is a good metabolizer or a poor metabolizer. Such diagnostic tests are performed so that a patient who is a "poor metabolizer" can be identified and protected against various drugs which he or she cannot metabolize properly.

Some of the foregoing points are documented in articles such as Guttendorf et al 1988, Kupfer et al 1984, and Koppel et al 1987, which discuss poor metabolizers; other points were gleaned from other articles, cited above, which discuss the general characteristics of cytochrome P450 enzymes.

In light of these facts and correlations, reports such as Broly et al 1989, which indicates that quinidine suppresses DM oxidation in liver cell preparations, are actually warnings calling attention to the fact that if a patient is taking quinidine, the patient becomes a high-risk "poor metabolizer" who must be protected against the dangers and risks that affect poor metabolizers. In addition, these articles warn doctors that if a patient is taking a drug such as quinidine, then the diagnostic test for identifying "poor metabolizers" will not give accurate results and should not be used.

The Applicant's analysis of the literature also disclosed another important factor. The primary oxidized metabolic product of dextromethorphan is dextrorphan, which is widely believed among neurologists to be active in exactly the same manner as dextromethorphan; both drugs reportedly are sigma agonists, NMDA antagonists, and calcium channel antagonists. Since the metabolite of DM is widely believed to have exactly the same neuronal activities as DM, neurologists and others had no motivation to try to use anti-oxidants to increase DM concentrations in the blood.

As further evidence of the absence of any interest among neurologists in using cytochrome P450 inhibitors to increase dextromethorphan concentrations in the blood of patients receiving DM, it should be noted that a number of recent studies have been performed to evaluate DM in patients suffering neurological diseases (e.g., Walker and Hunt 1989, Albers et al 1991, Applebaum et al 1991, and Askmark et al 1993). Although these researchers clearly recognized and discussed the problems caused by DM metabolism, none of their reports made any mention of or showed any interest in using quinidine or any other oxidation inhibitor to slow down the enzymatic degradation of DM.

Despite the relevant facts and prevailing beliefs in this field of research, the work by the Applicant has disclosed that co-administration of quinidine in conjunction with DM leads to at least two apparent therapeutic benefits (the suppression of emotional lability, and the treatment of dermatitis). These benefits were remarkably effective in the patients tested, but they were not detectable in any patients treated with dextromethorphan alone.

Accordingly, one object of this invention is to disclose that in patients who are "extensive metabolizers" of DM and who are suffering from severe dermatitis which does not respond to non-prescription drugs, DM can be administered in conjunction with an second compound (such as quinidine) which inhibits the DM-degrading oxidative activity of the debrisoquin hydroxylase enzyme, and the combined drug regimen can effectively and beneficially treat severe or intractable dermatitis in at least some patients.

Another object of this invention is to disclose that any of several compounds which are known to inhibit the DM-degrading oxidative activity of debrisoquin hydroxylase can be tested to determine whether they are pharmaceutically acceptable in a specific patient suffering from severe dermatitis. Using routine tests, a specific anti-oxidant compound can be identified which has minimal adverse effects in a specific patient who is in need of treatment. After a preferred anti-oxidant compound has been ideeentified for that patient, an optimal dosage of the anti-oxidant drug can be determined which will sustain maximal blood concentrations of DM in the patient. The selected compound can then be co-administered at the selected dosage, along with a suitable dosage of DM, to treat the dermatitis.

Another object of this invention is to disclose that DM, by itself, appears to be able to treat dermatitis in patients who are classified as "poor metabolizers" (i.e., in patients who lack a functioning debrisoquin hydroxylase enzyme). Since such patients do not have a functioning debrisoquin hydroxylase enzyme in the first place, they apparently will not require co-administration of any antioxidant drug in order to inhibit the oxidation and elimination of DM. In "poor metabolizer" patients, DM alone should have the same effects as a DM/antioxidant combination will have in "extensive metabolizer" patients.

These and other objects of the invention will become apparent from the following description of the invention.

It is also noted that the co-pending application Ser. No. 07/896,053, now abandoned, also invented by the Applicant, disclosed that the DM/antioxidant combination treatment has been shown to be effective in treating a variety of conditions which are tied together by a common thread: they involve unwanted nerve impulses. These conditions include (1) emotional lability as discussed above: (2) the itching and pain that accompany severe dermatitis; and, (3) at least one other other medically significant, otherwise-intractable condition that has been identified and treated with excellent results using a DM/antioxidant combination (this method of treatment is the subject of another patent application that is pending before the U.S. Patent and Trademark Office). Accordingly, the co-pending application Ser. No. 07/896,053, now abandoned, disclosed and claimed a general method of treating "unwanted nerve impulses" using a DM/antioxidant combination treatment. Those claims were restricted during examination, and they will become the subject of a divisional application; they are mentioned herein, and the teachings of co-pending application Ser. No. 07/896,053, now abandoned, are hereby incorporated by reference, to ensure copendency of that aspect of the disclosure.

SUMMARY OF THE INVENTION

This invention discloses a method for treating human patients suffering from dermatitis, particularly severe dermatitis which does not respond adequately to non-prescription drugs. Such patients are treated using dextromethorphan (DM), an antitussive agent normally used in cough syrup. If the patient is a so-called "extensive metabolizer," an antioxidant drug (such as quinidine) can be coadministered to inhibit the DM-degrading activity of debrisoquin hydroxylase, an enzyme that will rapidly convert DM into its metabolite, dextrorphan. This treatment has been shown to be highly effective in treating severe dermatitis, and in most patients this drug combination causes no significant adverse side effects.

DESCRIPTION OF THE PREFERRED EMBODIMENTS

This invention discloses a method for treating humans suffering from severe dermatitis. As used herein, "severe dermatitis" includes visible lesions and/or an itching or burning sensation on one or more epidermal surfaces, wherein the lesions or itching do not respond adequately to any non-prescription (over-the-counter) drug, lotion, or ointment. This method involves the use of dextromethorphan (DM), which is normally used as an antitussive agent in cough syrup, or a pharmaceutically acceptable salt or analog thereof.

In patients who have a functioning debrisoquin hydroxylase enzyme (such people are often referred to in the medical literature as "extensive metabolizers), the DM preferably should be co-administered along with an antioxidant drug which is pharmaceutically acceptable in the patient being treated and which inhibits the DM-oxidizing activity of one or more enzymes in the person being treated (presumably, debrisoquin hydroxylase or one or more other cytochrome P450 enzymes with an overlapping substrate range that includes DM). By inhibiting the enzymatic degradation of DM, the antioxidant drug increases the concentration of DM in the circulating blood, as disclosed in Examples 1-3. Increases in circulating blood concentrations can be evaluated by analyzing samples of either blood or urine, as described below. The antioxidant-mediated increase of DM concentration in the blood of an extensive metabolizer patient will directly increase the ability of DM to carry out functions which directly depend on the concentration of DM in the blood.

In dermatitis patients who are classified as "poor metabolizers" (such patients do not have a functioning debrisoquin hydroxylase enzyme; this population is believed to comprise roughly 7-10% of the adult Caucasian population), DM alone, in adequate quantities (such as a range of about 120 mg/day up to about 400 mg/day) is likely to be sufficient to treat dermatitis without requiring an antioxidant.

As discussed in the Background section, the activity of DM in suppressing nerve signals is believed to involve at least three and possibly more types of neuronal receptor. DM functions (1) as an agonist at sigma receptors, which are inhibitory; (2) as an antagonist at NMDA receptors, which are excitatory; and, (3) as an antagonist at neuronal calcium channels, which are excitatory. All of these neuronal interactions involve and presumably require direct contact of DM molecules with neurons. Accordingly, an increase in the concentration of DM in the blood, due to the presence of an antioxidant drug that suppresses oxidative degradation of DM, directly increases the ability of the circulating DM to exert its beneficial effects in extensive metabolizers.

Dextromethorphan is widely available in cough syrup formulations, at dosages up to about 120 mg/day for an adult, without a prescription. It is also available in pills, but only by prescription. It is usually administered for therapeutic purposes at dosages of about 150 mg/day or less, but it is sometimes tested for efficacy at dosages ranging up to about 300 mg/day or higher; such tests sometimes indicate that certain patients do not tolerate such levels well, but any adverse effects (such as dizziness or nausea) usually disappear quickly when the dosage is lowered, so DM can be tested safely at dosages ranging up to about 1000 mg/day in adults (or even higher, in adults who metabolize and eliminate DM relatively quickly). This invention anticipates DM dosages in the range of about 20 mg/day to about 400 mg/day, depending on factors such as the weight of the patient, the severity of the patient's problems, a patient's status as a potentially poor metabolizer, and the potency and dosage of the antioxidant agent selected for use in a specific patient who is an extensive metabolizer.

The terms "salt" and "analog" are used in their conventional pharmaceutical sense, and are limited to pharmacologically acceptable and therapeutically effective salts and analogs. The term "pharmacologically acceptable" embraces those characteristics which make a salt or analog suitable and practical for administration to humans; for example, such compounds must be sufficiently chemically stable under reasonable storage conditions to have an adequate shelf life, they must be physiologically acceptable when introduced into the body by a suitable route of administration, and they must not be addictive or cause unacceptable side effects. Acceptable salts can include alkali metal salts as well as addition salts of free acids or free bases. Acids that may be employed to form acid addition salts include inorganic acids (e.g., to form sulfate or chloride salts) as well as organic acids. Alkali metal salts or alkaline earth metal salts might include, for example, sodium, potassium, calcium or magnesium salts. All of these salts may be prepared by conventional means. Various salts of the compounds described herein which are currently in widespread pharmaceutical use are listed in sources such as *The Merck Index*. The constituent used to make a salt of an active drug discussed herein is not critical, provided that it is non-toxic and does not substantially interfere with the desired activity.

A pharmaceutical analog refers to a molecule that resembles a referent compound but which has been modified in a targeted and controlled manner to replace one or more components of the referent molecule with alternate moieties or other substituents which do not ionize readily, as occurs in salts; the analog-producing substituent also must not destroy a desired function exhibited by the referent molecule. Any coverage of claims which refer to salts or analogs of DM are limited to salts or analogs which (1) exhibit a suitable and desirable level of activity at one or more classes of neuronal receptors activated by DM, and (2) exert a substantial therapeutic effect against dermatitis when used as described herein.

In addition, although research into such analogs has not yet commenced, it is recognized by the Applicant that there may be one or more analogs of dextromethorphan, already known or hereafter discovered, which may be effective in treating severe dermatitis without being oxidatively degraded by debrisoquin hydroxylase; if such compounds can be identified through screening tests, they may provide effective treatment for extensive metabolizers without requiring co-administration of an antioxidant drug.

Administration of the drugs described herein can be by any method capable of introducing the compounds into the bloodstream. Although oral administration is the simplest and therefore preferred route of administration, parenteral injection can be used if desired. Although evaluation of topical formulations has not yet commenced, it is possible that the drugs described herein can be administered effectively in topical formulations such as lotions or ointments. Any such formulations may comprise a mixture of active compounds with pharmaceutically acceptable carriers or diluents.

Selection of a Suitable Antioxidant for a Specific Patient

The selection and dosage of a preferred antioxidant compound will vary between different patients, and will require individual attention by the physician in charge of treating a specific patient. Quinidine, which is normally used as an anti-arrhythmia drug for patients having certain types of cardiac conditions, is a potent inhibitor of the debrisoquin hydroxylase enzyme, and it has few other substantial activities (for example, it apparently does not have any tranquilizing, drowsiness-inducing, or other psychoactive properties). These traits will generally make it a preferred antioxidant for many patients.

However, quinidine is not pharmaceutically acceptable by all patients. During the Applicant's initial tests, minor to moderate side effects (such as drowsiness or fatigue, lightheadedness, or loss of appetite) were reported by several ALS patients, and a small percentage of the ALS patients who received both drugs over a prolonged period of time began to suffer cumulative side effects which gradually increased in severity until the medication was discontinued. In addition, one ALS patient apparently was allergic to quinidine and developed a rash and jaundice-like symptoms of liver dysfunction, and another ALS patient who showed no ill effects during tolerance tests on DM alone (up to 120 mg/day) or on quinidine alone displayed an idiosyncratic reaction to a combination of quinidine and 60 mg DM; during this episode, he displayed severe disorientation similar in some respects to the effects of phencyclidine, a potent NMDA antagonist that is sometimes illegally abused under the street name "angel dust".

In addition, people who are taking anti-arrhythmia drugs should not be given quinidine (which is itself a potent anti-arrhythmia drug), and some people who suffer from a heart condition known as a prolonged QT interval can even suffer cardiac arrest (which can be fatal) if given quinidine.

Despite the problems encountered in a small number of ALS patients, the large majority of ALS patients (and all control subjects who were not afflicted with ALS) reported no adverse side effects from a combination of DM with quinidine.

It should also be noted that the dosage of quinidine which provided a major increase in DM concentration in the blood of extensive metabolizers was only a fraction of the dosage normally used for anti-arrhythmia purposes. Quinidine dosages of 600–1200 mg/day are commonly taken by cardiac patients; by contrast, dosages of 150 mg/day were highly effective in increasing DM concentrations, and it is believed that lower dosages (such as 100 mg/day or 50 mg/day) are likely to be effective in at least some patients.

Since some people cannot tolerate quinidine, other antioxidants will be preferred for some extensive metabolizer patients who are suffering from severe dermatitis. A number of drugs have been identified as being effective in inhibiting debrisoquin hydroxylase; Inaba et al 1985 indicated that nortriptyline, chlorpromazine, domperidone, haloperidol, pipamperone, labetalol, metaprolol, oxprenolol, propranolol, timolol, mexiletine, quinine, diphenhydramine, ajmaline, lobeline, papaverine, and yohimbine all have significant in vitro activity in inhibiting debrisoquin hydroxylase. Inhibitors that reportedly were relatively potent included yohimbine, haloperidol, ajmaline, lobeline, and pipamperone; those drugs were reported by Inaba et al 1985 to have Michaelis-Menton inhibition ($K_i$) values ranging from 0.33 to 4, compared to a $K_i$ value of 0.06 for quinidine (a low $K_i$ value indicates a high level of potency). In addition, although it was not mentioned by Inaba et al, research by the Applicant indicated that fluoxetine (sold under the trademark "Prozac") is also effective in increasing DM concentrations in the blood.

In vitro inhibition tests do not guarantee that a particular antioxidant will be both effective and free of side effects in a specific patient. It is well known that different people have substantial variations in their oxidative enzymes. These differences are reflected on a gross level by the fact that some people are classified as "extensive metabolizers" while others are classified as "poor metabolizers". On a more subtle level, people have differing abilities to tolerate and metabolize alcohol, tobacco smoke, environmental contaminants, various drugs, and various illegal intoxicants. Any physician understands this as a routine aspect of medicine and metabolism; it is not very different from observing that some people are allergic to bee stings, pollen, or certain foods, while other people aren't.

Additional data showing the variability of oxidative enzyme activity between different people is provided in the data in Example 5, below. As shown in those data, patient M. C. showed an increase in the DM/DR ratio after administration of fluoxetine (Prozac). By contrast, patient J. K. did not show any such increase, and actually showed a drop in the DM/DR ratio after administration of fluoxetine. Similarly, patient P. S. showed an increase in DM/DRP after administration of propranolol (sold under the trademark Inderal); by contrast, patient F. O. showed a drop.

Accordingly, even though in vitro tests offer useful guidance in selecting candidate antioxidant compounds, the actual effects of an antioxidant compound in a specific patient with a unique genetic makeup and oxidative enzyme profile can be assessed only by testing the compound in that specific patient. This is not difficult and can be handled in a routine matter by physicians. Before prescribing any medicine, most physicians ask a patient whether he (or she) has ever tried that medicine before, whether he had any type of adverse reaction to it, and whether he has ever had any allergic reactions to any other medications. This is standard practice, and such caution is warranted when prescribing compounds known to reduce the activities of enzymes that normally help people metabolize and eliminate toxins. A physician who wishes to use a DM/antioxidant combination to treat dermatitis as described herein should run an initial tolerance test using a relatively low dose of a candidate antioxidant drug, to assess its safety and lack of side effects in a particular patient. If the drug does not induce any substantial adverse effects at that dosage, it can then be tested for both safety and efficacy in that patient, at a higher dosage.

Efficacy testing using a particular antioxidant combined with DM can be carried out using any of several methods. In one approach, a patient suffering from dermatitis is simply asked to report on the apparent effects of the DM/antioxidant combination. If the patient reports substantial relief from the dermatitis without any unacceptable side effects, then that combination can be used in that patient, and the physician can test varying dosages to optimize the dosage of each of the two drugs in that patient.

The second method involves sampling body fluids to compare the concentrations of DM and its primary metabolite, dextrorphan (DR). Although blood concentrations can be directly evaluated by drawing blood samples if desired, an easier and painless approach is to analyze urine samples. Blood or urine samples can be processed using methods such as high performance liquid chromatography (HPLC), as described in Example 5. Two distinct peaks will be displayed on the HPLC printout, one for DM and one for the DR metabolite. The height of each peak, or the area under each peak, will indicate the quantity of each compound in the blood or urine sample. The heights of the DM and DR peaks are then divided, to determine the DM/DR ratio. The ratio which occurs after administration of a candidate antioxidant drug is compared to the DM/DR ratio in the same patient under control conditions (i.e., before administration of any antioxidant). If a candidate antioxidant drug significantly increases the DM/DR ratio of an extensive metabolizer patient who is suffering from severe dermatitis, without causing unacceptable side effects, that antioxidant can be used in combination with DM to treat that patient.

Currently, quinidine and most of the other candidate antioxidant drugs are available only by prescription. It should be kept in mind also that any potent antioxidant will be of interest herein specifically because it can convert people with normal oxidative enzyme profiles into "poor metabolizers." Accordingly, the DM/antioxidant combinations disclosed herein are currently anticipated for use only under the supervision of a physician, to treat dermatitis which does not respond adequately to non-prescription drugs, lotions, or ointments.

However, it is recognized that dermatitis ranges in severity across an entire spectrum, and cannot be grouped simply into mild or severe cases. There are many thousands or even millions of cases of moderately severe dermatitis which cause substantial irritation and distress, which can be either continuous or intermittent. It is also recognized that as additional experience is gathered using prescription drugs to treat humans, doctors and regulatory officials often realize that a certain prescription drug is safe enough in the large majority of patients to allow over-the-counter sale and use in limited dosages or concentrations. Accordingly, a combination of DM and a relatively low, generally safe dosage of a selected antioxidant may be safe enough for over-the-counter sale and use to treat moderate dermatitis which does not respond adequately to other treatments.

Regardless of how it is sold, people using any oxidation inhibitors should be warned that such drugs suppress the body's ability to metabolize and eliminate certain types of drugs, environmental contaminants, and other compounds. Accordingly, anyone taking an oxidation inhibitor should be advised to discontinue the consumption of tobacco, alcohol, and non-essential drugs, especially drugs that suppress hepatic (liver) activity or oxidative enzymes. In addition, physicians prescribing antioxidants should be alerted to potential interactions between an antioxidant being prescribed, and other drugs which may not be tolerated well in the presence of that antioxidant. For example, quinidine (which is normally an anti-arrhythmia drug) should not be used in combination with other anti-arrhythmia drugs.

A doctor can determine optimal dosages of DM and a candidate antioxidant drug for a specific patient using routine procedures. Initial tolerance tests preferably should be conducted first, using relatively low dosages of DM alone, a candidate antioxidant alone, and the DM/antioxidant combination. If the tolerance tests do not indicate any unacceptable side effects, the doctor can test varying dosages of each drug and evaluate the patient's response to each dosage that is tested, to determine optimal dosages.

Tolerance tests for a candidate antioxidant drug should use low dosages, such as in the range of about 10% to about 50% of the daily dosage used for normal therapeutic purposes. For example, 120 mg/day is a common dosage when DM is used therapeutically as an antitussive agent, and that dosage has been approved by the FDA for over-the-counter sale and use by the general public; therefore, a tolerance test using 50–75 mg/day DM in combination with an antioxidant would be in the appropriate range. When quinidine is used as an anti-arrhythmia drug, 600 mg/day is a common dosage; therefore, a tolerance test could use 50 or 100 mg/day. A dosage of 80 mg/day is common when fluoxetine (Prozac) is used as an antidepressant; therefore, a tolerance test could use 20 or 40 mg/day. Additional information on therapeutic and tolerance test dosages is available from manufacturers and in texts such as the *Physician's Desk Reference*.

EXAMPLES

Example 1

Urinary DM/DR Ratios

Since the research that led to this invention was done by a neurologist who was initially interested in finding out whether DM might be able to retard the progress of ALS, the initial studies were done on patients suffering from ALS, most of whom are adults more than 50 years old. No differences were detected in the metabolism of DM in ALS patients, compared to reported findings involving adults who do not have ALS and to one-day tests involving healthy volunteers as a control population.

Six patients suffering from ALS were administered orally a single 60 mg dextromethorphan dose. Several hours later, a urine sample was collected, and the urine concentrations of dextromethorphan (DM) and dextrorphan (DR) were measured as described below to determine a DM/DR ratio. A low DM/DR ratio indicates that DM is being rapidly oxidized to the DR metabolite in that body of that patient. In a different week, 60 mg of DM and 150 mg of quinidine were orally administered to the same patients, and urinary DM and DR levels and DM/DR ratios were determined again.

DM and DR urinary levels without quinidine were determined by adding 40 mg of thebaine as an internal standard to 1 mL of urine. To this was added 2000 units of beta-glucuronidase in 1 mL of acetate buffer (0.1M, pH 5.0). The mixture was incubated for 18 hours at 37° C. and then extracted by adding 1 mL of phosphate buffer (pH 12, 0.10M) and 7 mL of n-butanol/hexane (10:90 v/v). After mixing and centrifugation, the organic layer was transferred to a clean tube and acidified with 400 uL of 0.01 N HCL. 20 microliters (uL) of aqueous phase was injected into a high performance liquid chromatography (HPLC) system. The HPLC used a phenyl column equilibrated with a mobile phase of acetonitrile:water (51:49, v/v) containing 10 mM $KHPO_4$, 10 mM hexane sulfonic acid, pH 4.0 (flow rate 1.2 mL/min). Detection of thebaine, dextromethorphan and dextrorphan was achieved by fluorescence (Kratos FS-980 Fluorometer) with an excitation wavelength of 228 nm and no emission cutoff filter.

A gas chromatograph/mass spectroscopy (gc/ms) assay was employed for determining dextromethorphan and dextrorphan levels in the presence of quinidine. Briefly, 0.5 ml urine samples were spiked with 500 nanograms (ng) of dimethacrine. The urine pH was adjusted to 5.0 with 0.1M acetate buffer (usually about 1.0 ml), and beta-glucuronidase was added (2000 units/ml urine). The mixture was incubated and shaken at 37° C. for 18 hours. The urine was subsequently adjusted to pH 10-11 with 1.0 mL of phosphate buffer, and the urine was extracted with 5 mL of dichloromethane. The dichloromethane extract was evaporated under nitrogen, reconstituted in 300 uL of BSTFA and injected onto a gc-ms analyzer equipped with a capillary SE-30 column. Gas chromatographic conditions were: injector and transfer line temperature 250° C., oven 70° C. to 260° C. at 20° C. per minute, and source temperature 180° C. Detection was by selected ion monitoring at m/z 271 for dextromethorphan, 294 for the internal standard, and 329 for dextrorphan. Typical standard curves for dextromethorphan and dextrorphan were provided. Assay sensitivity was 100 ng/ml for dextromethorphan and 400 ng/ml for dextrorphan.

The results, in Table 1, indicated that quinidine is a potent inhibitor of dextromethorphan metabolism. The DM/DR ratio in all test subjects was increased by at least 2 and usually more than 3 orders of magnitude.

TABLE 1

| Patient # | URINARY DM/DR RATIOS | |
|---|---|---|
| | DM/DR Ratio, no quinidine | DM/DR Ratio, 150 mg quinidine |
| 1 | 0.0048 | 4.090 |
| 2 | 0.0220 | 3.460 |
| 3 | 0.0002 | 0.635 |
| 4 | 0.0003 | 0.420 |
| 5 | <0.0002 | 0.631 |
| 6 | 0.054 | 3.29 |

Followup tests were done on more than 50 people, including ALS patients and healthy controls who volunteered for one-day tests. The ALS patients received DM and quinidine on a daily basis over several weeks, while control subjects received only a single dose of each drug. The results were very similar to the data contained in Table 1.

Example 2

Plasma Concentrations of DM

Five patients were orally administered 120 mg of DM, with no co-administration of quinidine. Between 10 and 12 hours later, blood was sampled, blood plasma was isolated by centrifugation, and the plasma was analyzed to determine the DM concentration using the thebaine/HPLC method.

During a different week, the same patients were orally administered 60 mg of DM (half the control dosage) and 150 mg of quinidine. Between 10 and 12 hours later, blood was sampled and the plasma was analyzed for DM using thebaine/HPLC.

The results, in Table 2, indicate that quinidine causes a major increase in the concentration of DM in the blood plasma.

TABLE 2

| EFFECTS OF QUINIDINE ON PLASMA DM | | | |
|---|---|---|---|
| PATIENT (MG/DAY) | DM DOSE | DM PLASMA LEVEL | QUINIDINE DOSE |
| 1 | 120 MG/DAY | NOT DETECTABLE | 0 |
| | 60 MG ONCE | 33 NG/ML | 150 |
| 2 | 120 MG/DAY | 9.3 NG/ML | 0 |
| | 60 MG ONCE | 29.7 NG/ML | 150 |
| 3 | 120 MG/DAY | NOT DETECTABLE | 0 |
| | 60 MG ONCE | 29.0 NG/ML | 150 |
| 4 | 120 MG/DAY | 16.5 NG/ML | 0 |
| | 60 MG ONCE | 28.8 NG/ML | 150 |
| 5 | 120 MG/DAY | 6.05 NG/ML | 0 |
| | 60 MG ONCE | 45.6 NG/ML | 150 |

Subsequently, plasma levels were determined for about 15 other ALS patients who received dextromethorphan and quinidine over a prolonged period of time. The results were very similar to the data in Table 2.

Example 3

Dose-Response Study

Figure 2:
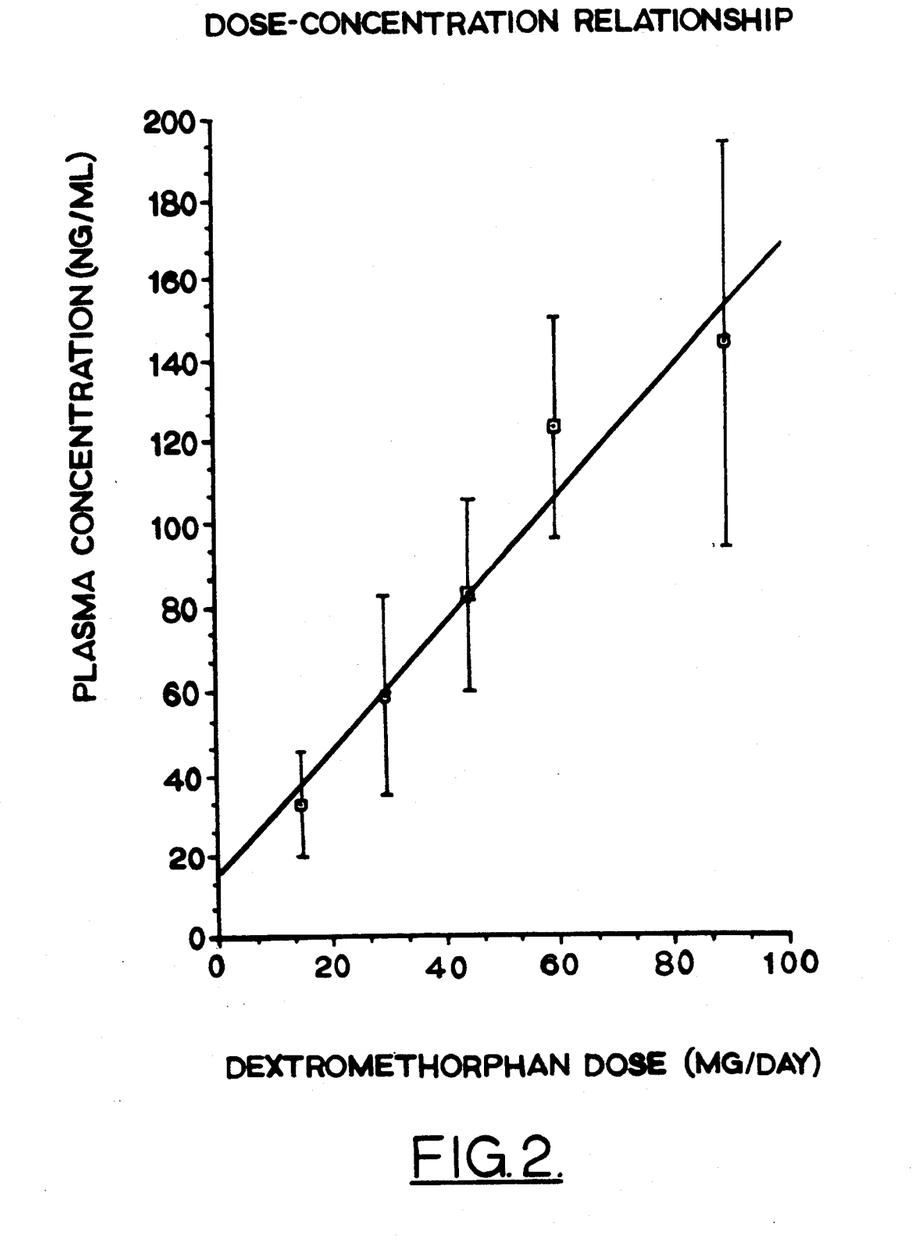
FIG. 2 is a graph depicting the relationship between DM oral dosages and DM plasma concentrations in patients receiving 150 mg/day of quinidine.

Additional studies were undertaken using a range of dosages of DM to establish a dose-response curve that correlates the quantity of DM orally administered to a patient with blood plasma concentrations 10 to 12 hours later (determined as described in Example 2). All patients received 150 mg of quinidine daily. The results of those studies are shown in graphical form in FIG. 2, with mean values shown as open squares and standard deviation ranges shown by vertical bars. The ascending line through the median values is a linear approximation; a curve based on more extensive data would probably show a horizontal asymptote.

Since the oxidation of DM to the specific metabolite dextrorphan is due to the enzyme debrisoquin hydroxylase, the results of the tests described in the foregoing Examples indicate that if DM is co-administered with a second drug that inhibits the oxidative activity of debrisoquin hydroxylase, then DM circulation in the blood is increased and prolonged, without causing severe side effects.

Example 4

Suppression of Dermatitis

During an initial examination, the Applicant discovered that patient BT, a Caucasion female in her 60's who was suffering from ALS, suffered from a severe dermatologic condition involving lesions which appear in relatively small purplish patches ("polygonal papules"). Her condition had recently been diagnosed as lichen planus. The etiology is unknown, although a variety of drugs reportedly can aggravate this condition. The patient reported that the lesions were severely itchy, and she had been suffering from it for roughly ten years. She had been prescribed a number of drugs (including various steroids such as prednisone) in an effort to control the itching; the most recent prescription was "Doxepin," a tricyclic antidepressant. None of those agents offered much relief.

The patient began an initial treatment of quinidine alone (150 mg/day) for a week. After it had been established that she did not have an adverse reaction, she began to receive DM as well, beginning at 30 mg/day, and increasing after 1 month to 120 mg/day.

During the second monthly visit after beginning the DM/quinidine treatment, the Applicant found that the patient had obtained an almost total cessation of any itching sensations, with partial resolution of her lesions. A follow-up exam some weeks later indicated that the patient's skin lesions had almost completely healed with no apparent evidence of scar tissue.

After seeing this result, the Applicant disclosed his finding to a dermatologic specialist at a nearby university and suggested that a confirmatory study be done. The specialist carried out a preliminary test involving DM and quinidine on a male Caucasian who suffered from severe but intermittent dermatitis. Due to the intermittent nature of the dermatitis, the results of a single round of testing could not be conclusively attributed to the DM/antioxidant combination; nevertheless, the results from this test indicated a substantial improvement in the patient's condition when the DM/antioxidant combination was administered.

Example 5

Preliminary Analysis of Other Antioxidants

While carrying out his initial tests involving quinidine as an antioxidant in ALS patients, the Applicant observed some unusual results in one female patient. Further investigation disclosed that the patient was taking fluoxetine (Prozac) as an antidepressant, and that fluoxetine apparently can suppress the oxidative activity of the debrisoquin hydroxylase enzyme, albeit at a potency substantially below that of quinidine. This result, coupled with the data listed in Inaba et al 1985, indicated that various drugs might have sufficient potency as antioxidants to increase and prolong the concentrations of DM in the circulating blood of extensive metabolizers.

To further evaluate that possibility, the Applicant arranged for chemical analyses of urine samples, using HPLC, in the labs of an independent investigator. Regrettably, not all of the desired controls were tested during the first round of tests, and some of the control samples were inadvertently discarded by a research assistant; in addition, not all of the candidate compounds that have been identified have been tested. Therefore, the data provided in Table 3 must be regarded as only preliminary. Nevertheless, these data indicate that (1) due to enzymatic differences, not all patients respond identically or uniformly to any particular antioxidant, but (2) any of several known candidate compounds can, in at least some patients, cause a significant reduction in the rate of oxidation of dextromethorphan.

TABLE 3
EFFECTS OF VARIOUS ANTIOXIDANTS ON DM METABOLISM IN SPECIFIC PATIENTS

| Patient's initials | DM/DR ratio, no antioxidant | DM/DR ratio (antioxidant) |
| --- | --- | --- |
| T. S. | 0.02 | 0.09 (quinine sulfate) |
| G. M. | 0.00 | 0.05 (quinine sulfate) |
| B. B. | 0.06 | 0.01 (disulfiram) |
| J. B. | 0.06 | 0.08 (disulfiram) |
| M. C. | 0.00 | 0.11 (fluoxetine) |
| J. K. | 0.03 | 0.00 (fluoxetine) |
| P. S. | 0.00 | 0.02 (propranolol) |
| F. O. | 0.02 | 0.00 (propranolol) |

Thus, there has been described a method of treating dermatitis, particularly severe forms of dermatitis which do not respond adequately to non-prescription medicine. Although this method has been described with reference to certain specific embodiments, those skilled in the art will recognize that various modifications can be made to those particular embodiments without departing from the spirit or teachings of this invention. Such modifications are considered to be within the scope and coverage of the claims below.

REFERENCES

Albers, G. W., et al, "Safety and tolerance of oral dextromethorphan in patients at risk for brain ischemia," Stroke 22: 1075–1077 (1991)

Applebaum, J. S., et al, "Dextromethorphan in the treatment of ALS: A pilot study," Abstract number 960S (page 393) in Neurology 41 (Suppl. 1), March 1991

Askmark, H., et al, "A pilot trial of dextromethorphan in ALS," J. Neurol. Neurosurg. Psychiatry 56:197–200 (1993)

Brinn, R., et al, "Sparteine oxidation is practically abolished in quinidine-treated patients," Br. J. Clin. Pharmacol. 22: 194–197 (1986)

Broly, F., et al, "Effect of quinidine on the dextromethorphan O-methylase activity of microsomal fractions from human liver," Br. J. Clin. Pharmacol. 28:29–36 (1989)

Brosen, K., et al, "Extensive metabolizers of debrisoquin become poor metabolizers during quinidine treatment," Pharmacol. Toxicol. 60:312–314 (1987)

Carpenter, C. L., et al, "Dextromethorphan and dextrorphan as calcium channel antagonists," Brain Research 439: 372–375 (1988)

Choi, D. W., "Dextrorphan and dextromethorphan attenuate glutamate neurotoxicity," Brain Res. 402: 333–336 (1987)

Craviso, G. L., and Musacchio, J. M., "High affinity dextromethorphan binding sites in guinea pig brain," Mol. Pharmacol. 23: 619–640 (1983)

Dayer, R., et al, "Dextromethorphan O-demethylation in liver microsomes . . . " Clin. Pharmacol. Ther. 45: 34–40 (1989)

Feeser et al, Neurosci. Letters 86: 340–345 (1988)

Ferkany et al, Eur. J. Pharmacol. 151:151–154 (1988)

Fonne-Pfister et al, Biochem. Biophys. Res. Communic. 148: 1144–1150 (1987)

Guttendorf, R. J., et al, "Simplified phenotyping with dextromethorphan by thin-layer chromatography: Application to clinical laboratory screening for deficiencies in oxidative drug metabolism," *Ther. Drug. Monit.* 10: 490–498 (1988)

Inaba, T., et al, "In vitro inhibition studies of two isozymes of human liver cytochrome P-450," *Drug Metabolism and Disposition* 13: 443–447 (1985)

Inaba, T., et al, "Quinidine: Potent inhibition of sparteine and debrisoquin oxidation in vivo," *Br. J. Clin Pharmacol* 22: 199–200 (1986)

Koppel, C., et al, "Urinary metabolism of dextromethorphan in man," *Arzneim.-Forsch/Drug Research* 37: 1304–1306 (1987)

Koyuncuoglu & Saydam, *Intnl. J. Clin. Pharmacol. Ther. Tox.* 28: 47–152 (1990)

Kupfer, A., et al, "Dextromethorphan as a safe probe for debrisoquin hydroxylation polymorphism," *Lancet* ii: 517–518 (1984)

Leander, *Epilepsy Res.* 4:28–33 (1989)

Musacchio, J. M., et al, "High affinity dextromethorphan binding sites in the guinea pig brain," *J. Pharmacol. Exp. Ther.* 247: 424–431 (1988)

Nielsen, M. D., et al, "A dose-effect study of the in vivo inhibitory effect of quinidine on sparteine oxidation in man," *Br. J. Clin. Pharmacol.* 29:299–304 (1990)

Niznik et al, *Arch. Biochem. Biophys.* 26:424–432 (1990)

Prince & Feeser, *Neurosci. Letters* 85:291–296 (1988)

Ramachander, G., et al, "Determination of dextrorphan in plasma and evaluation of bioavialability dextromethorphan hydrobromide in humans," *J. Pharm. Sci.* 66: 1047–1048 (1977)

Rodd, E. H., *Chemistry of Carbon Compounds* (Elsevier Publ., New York, 1960)

Steinberg, G. K., et al, "Delayed treatment with dextromethorphan and dextrorphan reduces cerebral damage after transient focal ischemia," *Neurosci. Letters* 89: 193–197 (1988)

Tortella et al, *TIPS* 10:501–507 (1989)

Vettican, S. J., et al, "Phenotypic differences in dextromethorphan metabolism," *Pharmaceut. Res.* 6: 13–19 (1989)

Walker, E. O., and Hunt, V. P., "An open label trial of dextromethorphan in Huntington's Disease," *Clin. Neuropharmacol.* 12: 322–330 (1989)

Wong, B. Y., et al, "Dextrorphan and dextromethorphan, common antitussives, are antiepileptic and antagonize NMDA in brain slices," *Neurosci. Letters* 85:21–26 (1988)

I claim:

1. A method of treating dermatitis in humans, comprising administering to a patient suffering from dermatitis which does not respond adequately to non-prescription drugs a therapeutically effective quantity of a drug selected from the group consisting of:
   (a) dextromethorphan, and
   (b) pharmaceutically acceptable salts and analogs of dextromethorphan which are effective in treating dermatitis.

2. The method of claim 1 wherein the patient being treated is classified as a "poor metabolizer" whose enzymes cannot rapidly convert dextromethorphan into dextrorphan.

3. A method of treating dermatitis in a human patient, comprising administering to a patient who is an extensive metabolizer of dextromethorphan, and who is suffering from dermatitis which does not respond adequately to non-prescription drugs, a combination of dextromethorphan or a pharmaceutically acceptable salt or analog thereof, and an antioxidant drug which significantly inhibits enzymatic oxidation of dextromethorphan in that patient and which is pharmaceutically acceptable to that patient, at therapeutically effective dosages for each compound which allow the antioxidant drug to significantly inhibit enzymatic oxidation of the dextromethorphan in the body of the patient and which allow the dextromethorphan or the salt or analog thereof to provide substantial relief from the dermatitis.

4. The method of claim 3 wherein the antioxidant drug is selected from the group consisting of quinidine, quinine, and fluoxetine, and pharmaceutically acceptable salts and analogs thereof which inhibit the enzymatic degradation of dextromethorphan.

5. The method of claim 4 wherein quinidine is administered to a patient at a dosage not exceeding about 150 milligrams per day.

* * * * *